US012023318B2

(12) United States Patent
Kinsler

(10) Patent No.: US 12,023,318 B2
(45) Date of Patent: Jul. 2, 2024

(54) THERAPY FOR INFLAMMATORY LINEAR VERRUCOUS EPIDERMAL NEVUS (ILVEN)

(71) Applicant: UCL Business Ltd, London (GB)

(72) Inventor: Veronica Kinsler, London (GB)

(73) Assignee: UCL BUSINESS LTD, London (GB)

( * ) Notice: Subject to any disclaimer, the term of this patent is extended or adjusted under 35 U.S.C. 154(b) by 645 days.

(21) Appl. No.: 17/270,630

(22) PCT Filed: Aug. 29, 2019

(86) PCT No.: PCT/GB2019/052409
§ 371 (c)(1),
(2) Date: Feb. 23, 2021

(87) PCT Pub. No.: WO2020/044045
PCT Pub. Date: Mar. 5, 2020

(65) Prior Publication Data
US 2021/0260024 A1    Aug. 26, 2021

(30) Foreign Application Priority Data

Aug. 29, 2018 (GB) ..................... 1814036

(51) Int. Cl.
*A61K 31/37* (2006.01)
*A61K 9/00* (2006.01)
*A61K 31/575* (2006.01)
*A61K 45/06* (2006.01)

(52) U.S. Cl.
CPC ............ *A61K 31/37* (2013.01); *A61K 9/0014* (2013.01); *A61K 31/575* (2013.01); *A61K 45/06* (2013.01)

(58) Field of Classification Search
CPC .................................. A61P 3/00; A61P 17/00
See application file for complete search history.

(56) References Cited

U.S. PATENT DOCUMENTS 5,179,086 A    1/1993  Flender
2020/0345678 A1  11/2020  Kurban et al.

FOREIGN PATENT DOCUMENTS

| EP | 2425831 A1 | 3/2012 |
| ES | 2192988 A1 | 10/2003 |
| WO | WO-2001/078706 A2 | 10/2001 |
| WO | WO-2003/072013 A2 | 9/2003 |
| WO | WO-2004/026297 A1 | 4/2004 |
| WO | WO-2012/150892 A1 | 11/2012 |
| WO | 2021123750 A1 | 6/2021 |

OTHER PUBLICATIONS

Garcias-Ladaria, J. et al. "Epidermal nevi and related syndromes—Part 1: Keratinocytic nevi", Actas Dermosifiliogr., 2018; 109(8): 677-686. (Year: 2018).*

Atzmony, L. et al. "ILVEN encompasses a spectrum of inflammatory mosaic disorders", Pediatric Dermatology, Nov./Dec. 2022, vol. 39, Issue 6. p. 903-907, abstract.*
Dand et al. (Nov. 1, 2017) "Exome-wide Association Study Reveals Novel Psoriasis Susceptibility Locus at Tnfsf15 and Rare Protective Alleles in Genes Contributing to Type I Ifn Signalling", Human Molecular Genetics, 26(21):4301-4313.
Grange, et al. (Feb. 14, 2000) "CHILD Syndrome Caused by Deficiency of 3beta-hydroxysteroid-delta8, Delta7-isomerase", American Journal of Medical Genetics, 90(4):328-335.
International Search Report and Written Opinion for Application No. PCT/GB2020/053216, dated Mar. 29, 2021, 17 pages.
Namazi et al. (Jun. 2004) "Statins: Novel Additions to the Dermatologic Arsenal?", Experimental Dermatology, 13(6):337-339.
Pietrzak et al. (Mar. 2019) "Serum Lipid Metabolism in Psoriasis and Psoriatic Arthritis—an Update", Archives of Medical Science, 15(2):369-375.
United Kingdom Search Report for Application No. GB1918752.5, dated Jun. 17, 2020, 2 pages.
Abbasi N, Fangman WL, Rosenman KS, Schaffer JV. ILVEN-like persistent psoriasiform dermatitis confined to a congenital Becker nevus. Pediatric dermatology 2008;25:390-1.
Adrian RM, Baden HP. Analysis of epidermal fibrous proteins in inflammatory linear verrucous epidermal nevus. Archives of dermatology 1980;116:1179-80.
Akelma, A.Z., et al., A Diagnostic Dilemma: Inflammatory Linear Verrucous Epidermal Nevus versus Linear Psoriasis. The Journal of Pediatrics, 2013. 162(4): p. 879-879.e1.
Al-Enezi, S., et al., Inflammatory linear verrucous epidermal nevus and arthritis: a new association. J Pediatr, 2001. 138(4): p. 602-4.
Altman J, Mehregan AH. Inflammatory linear verrucose epidermal nevus. Archives of dermatology 1971;104:385-9.
Benton JM, Brown PE, Church RE. The serum-cholesterol in psoriasis. Lancet 1963;1:583-4.
Bergqvist C, et al: CHILD syndrome: A modified pathogenesis-targeted therapeutic approach. Am J Med Genet A. Mar. 2018;176(3):733-738.
Bohm I, Bieber T, Bauer R. [Successful therapy of an ILVEN in a 7-year-old girl with calcipotriol]. Der Hautarzt; Zeitschrift fur Dermatologie, Venerologie, und verwandte Gebiete 1999;50:812-4.
Brauchli YB, Jick SS, Meier CR. Statin use and risk of first-time psoriasis diagnosis. Journal of the American Academy of Dermatology 2011;65:77-83.
Choate KA, Topical cholesterol/lovastatin for the treatment of porokeratosis: a pathogenesis-directed therapy, Journal of the American Academy of Dermatology (2019).
Davidovici, B.B., et al., Psoriasis and systemic inflammatory diseases: potential mechanistic links between skin disease and co-morbid conditions. J Invest Dermatol, 2010. 130(7): p. 1785-96.

(Continued)

*Primary Examiner* — Gina C Justice
(74) *Attorney, Agent, or Firm* — Mintz Levin Cohn Ferris Glovsky and Popeo, P.C.

(57) ABSTRACT

The present invention provides a pharmaceutical composition which comprises: (a) an HMG-CoA reductase inhibitor; and (b) cholesterol or a pharmaceutically acceptable precursor thereof; for use in treating Inflammatory Linear Verrucous Epidermal Nevus (ILVEN).

15 Claims, No Drawings

(56) References Cited

OTHER PUBLICATIONS

De Jong E, Rulo HF, van de Kerkhof PC. Inflammatory linear verrucous epidermal naevus (ILVEN) versus linear psoriasis. A clinical, histological and immunohistochemical study. Acta dermato-venereologica 1991;71:343-6.
De Lucia M et al: Genetic variant in the NSDHL gene in a cat with multiple congenital lesions resembling inflammatory linear verrucous epidermal nevi. Vet Dermatol. Feb. 2019; 30(1):64-e18. Epub Nov. 25, 2018.
Dowlatshahi, E.A., et al., The prevalence and odds of depressive symptoms and clinical depression in psoriasis patients: a systematic review and meta-analysis. J Invest Dermatol, 2014. 134(6): p. 1542-51.
Dupre A, Christol B. Inflammatory linear verrucose epidermal nevus. A pathologic study. Archives of dermatology 1977;113:767-9.
Egeberg A, Riis Hansen P. Does treatment with statins protect against psoriasis? The British journal of dermatology 2015;173:327-8.
Egesi A, Sun G, Khachemoune A, Rashid RM. Statins in skin: research and rediscovery, from psoriasis to sclerosis. J Drugs Dermatol 2010;9:921-7.
Elias, P.M., et al., Basis for abnormal desquamation and permeability barrier dysfunction in RXLI. J Invest Dermatol, 2004. 122(2): p. 314-9.
Fleischer, A.B., Jr., et al., Patient Measurement of Psoriasis Disease Severity with a Structured Instrument. J Investig Dermatol, 1994. 102(6): p. 967-969.
Fox, B.J. and N.A. Lapins, Comparison of treatment modalities for epidermal nevus: a case report and review. J Dermatol Surg Oncol, 1983. 9(11): p. 879-85.
Gara A, Estrada E, Rothman S, Lorincz AL. Deficent Cholesterol Esterifying Ability of Lesion-Free Skin Surfaces in Psoriatic Individuals. The Journal of investigative dermatology 1964;43:559-64.
Ghazizadeh R, Tosa M, Ghazizadeh M. Clinical improvement in psoriasis with treatment of associated hyperlipidemia. Am J Med Sci 2011;341:394-8.
Goldman K, Don PC. Adult onset of inflammatory linear verrucous epidermal nevus in a mother and her daughter. Dermatology 1994; 189:170-2.
Grange DK, Kratz LE, Braverman NE, Kelley RI. Child syndrome caused by deficiency of 3beta-hydroxysteroid-delta8, delta7-isomerase. American journal of medical genetics 2000;90:328-35.
Griffiths, C.E. and J.N. Barker, Pathogenesis and clinical features of psoriasis. Lancet, 2007.
Groesser, L., et al., Postzygotic HRAS and KRAS mutations cause nevus sebaceous and Schimmelpenning syndrome. Nat Genet, 2012.
Hamm H, Happle R. Inflammatory linear verrucous epidermal nevus (ILVEN) in a mother and her daughter. American journal of medical genetics 1986;24:685-90.
Happle R, Koch H, Lenz W. The CHILD syndrome. Congenital hemidysplasia with ichthyosiform erythroderma and limb defects. European journal of pediatrics 1980;134:27-33.
Happle R, Mittag H, Kuster W. The CHILD nevus: a distinct skin disorder. Dermatology 1995;191:210-6.
Happle R. Child naevus is not ILVEN. Journal of medical genetics 1991;28:214.
Happle R. Ptychotropism as a cutaneous feature of the CHILD syndrome. Journal of the American Academy of Dermatology 1990;23:763-6.
Happle R. Superimposed linear psoriasis: a historical case revisited. J Dtsch Dermatol Ges 2011;9:1027-8; discussion 9.
Happle, R., Linear psoriasis and ILVEN: is lumping or splitting appropriate? Dermatology, 2006. 212(2): p. 101-2.
Happle, R., What is a nevus? A proposed definition of a common medical term. Dermatology, 1995. 191(1): p. 1-5.
Hattori, K., et al., Interferon gamma induces steroid sulfatase expression in human keratinocytes. Biol Pharm Bull, 2012. 35(9): p. 1588-93.
Hofer, T., Does inflammatory linear verrucous epidermal nevus represent a segmental type 1/type 2 mosaic of psoriasis? Dermatology, 2006. 212(2): p. 103-7.
Hugh J, Van Voorhees AS, Nijhawan RI, Bagel J, Lebwohl M, Blauvelt A et al. From the Medical Board of the National Psoriasis Foundation: The risk of cardiovascular disease in individuals with psoriasis and the potential impact of current therapies. Journal of the American Academy of Dermatology 2014;70:168-77.
Hwang, Y.J. and H.J. Jung, Serum levels of LL-37 and inflammatory cytokines in plaque and guttate psoriasis. 2014. 2014: p. 268257.
International Search Report and Written Opinion for International PCT Application No. PCT/GB2019/052409, dated Oct. 24, 2019 (12 pages).
Ito M, Shimizu N, Fujiwara H, Maruyama T, Tezuka M. Histopathogenesis of inflammatory linear verrucose epidermal naevus: histochemistry, immunohistochemistry and ultrastructure. Archives of dermatological research 1991;283:491-9.
Ju YS, Martincorena I, Gerstung M, Petljak M, Alexandrov LB, Rahbari R et al. Somatic mutations reveal asymmetric cellular dynamics in the early human embryo. Nature 2017;543:714-8.
Kay LJ, P.-J.J., Walker DJ, The prevalence and impact of psoriasis and psoriatic arthritis in the primary care population in North East England. Arthritis Rheum 1999. 42 (Suppl): p. 299.
Khalil S, Bardawil T, Saade S, Chedraoui A, Ramadan N, Hasbani DJ, Abbas O, Nemer G, Rubeiz N, Kurban M. Use of Topical Glycolic Acid Plus a Lovastatin-Cholesterol Combination Cream for the Treatment of Autosomal Recessive Congenital Ichthyoses. JAMA Dermatol. Nov. 1, 2018;154(11):1320-1323.
Kinsler VA, Larue L. The patterns of birthmarks suggest a novel population of melanocyte precursors arising around the time of gastrulation. Pigment cell & melanoma research 2017.
Kinsler, V.A., et al., Multiple congenital melanocytic nevi and neurocutaneous melanosis are caused by postzygotic mutations in codon 61 of NRAS. J Invest Dermatol, 2013. 133(9): p. 2229-36.
Kinsler, V.A., et al., Next-generation sequencing of nevus spilus-type congenital melanocytic nevus: exquisite genotype-phenotype correlation in mosaic RASopathies. J Invest Dermatol, 2014. 134(10): p. 2658-60.
Kiritsi D et al: Targeting epidermal lipids for treatment of Mendelian disorders of cornification. Orphanet J Rare Dis. Mar. 7, 2014;9:33.
Lee SH, Rogers M. Inflammatory linear verrucous epidermal naevi: a review of 23 cases. The Australasian journal of dermatology 2001;42:252-6.
Li S, Ganguli-Indra G, Indra AK. Lipidomic analysis of epidermal lipids: a tool to predict progression of inflammatory skin disease in humans. Expert Rev Proteomics 2016;13:451-6.
Lykkesfeldt, G., A.E. Lykkesfeldt, and N.E. Skakkebaek, Steroid sulphatase in man: a non inactivated X-locus with partial gene dosage compensation. Hum Genet, 1984. 65(4): p. 355-7.
Ma C, Harskamp CT, Armstrong EJ, Armstrong AW. The association between psoriasis and dyslipidaemia: a systematic review. The British journal of dermatology 2013;168:486-95.
Menni, S., et al., Inflammatory linear verrucous epidermal nevus (ILVEN) and psoriasis in a child? Int J Dermatol, 2000. 39(1): p. 30-2.
Moll, J.M.H. and V. Wright, Psoriatic arthritis. Seminars in Arthritis and Rheumatism, 1973. 3(1): p. 55-78.
Mosiewicz J, Pietrzak A, Chodorowska G, Trojnar M, Szepietowski J, Reich K et al. Rational for statin use in psoriatic patients. Archives of dermatological research 2013;305:467-72.
Moss C, Burn J. Child + ILVEN = PEN or PENCIL. Journal of medical genetics 1990;27:390-1.
Nestle, F.O., D.H. Kaplan, and J. Barker, Psoriasis. N Engl J Med, 2009. 361(5): p. 496-509.
Nguyen, V., et al., Cutaneous manifestations of Costello syndrome. Int.J.Dermatol., 2007. 46(1): p. 72-76.
O'Neill, P. and P. Kelly, Postal questionnaire study of disability in the community associated with psoriasis. Bmj, 1996. 313(7062): p. 919-21.

(56) References Cited

OTHER PUBLICATIONS

Oram, Y., et al., Bilateral inflammatory linear verrucous epidermal nevus associated with psoriasis. Cutis, 1996. 57(4): p. 275-8.
Ozdemir M, Balevi A, Esen H. An inflammatory verrucous epidermal nevus concomitant with psoriasis: treatment with adalimumab. Dermatology online journal 2012;18:11. https://escholarship.org/uc/item/7ts7s0st.
Rakheja D, Boriack RL. Precholesterol sterols accumulate in lipid rafts of patients with Smith-Lemli-Opitz syndrome and X-linked dominant chondrodysplasia punctata. Pediatr Dev Pathol. 2008;11(2):128-132.
Renner R, Colsman A, Sticherling M. ILVEN: is it psoriasis? Debate based on successful treatment with etanercept. Acta dermatovenereologica 2008;88:631-2.
Rulo HF, van de Kerkhof PC. Treatment of inflammatory linear verrucous epidermal nevus. Dermatologica 1991;182:112-4.
Seminara, N.M., et al., Validity of The Health Improvement Network (THIN) for the study of psoriasis. Br J Dermatol, 2011. 164(3): p. 602-9.
Sengupta S, Das JK, Gangopadhyay A. Naevoid Psoriasis and ILVEN: Same Coin, Two Faces? Indian journal of dermatology 2012;57:489-91. https://www.ncbi.nlm.nih.gov/pmc/articles/PMC3519259/.
Shapiro, L.J., et al., Molecular studies of deletions at the human steroid sulfatase locus. Proceedings of the National Academy of Sciences, 1989. 86(21): p. 8477-8481.
Shapiro, L.J., The Metabolic Basis of Inherited Disease. 1983: McGraw-Hill, Inc. New York.
Sommer, D.M., et al., Increased prevalence of the metabolic syndrome in patients with moderate to severe psoriasis. Arch Dermatol Res, 2006. 298(7): p. 321-8.
Soodgupta D, Kaul D, Kanwar AJ, Parsad D. Modulation of LXR-$\alpha$? and the effector genes by Ascorbic acid and Statins in psoriatic keratinocytes. Mol Cell Biochem. Dec. 2014;397(1-2):1-6.
Sotiriadis, D., et al., Is inflammatory linear verrucous epidermal naevus a form of linear naevoid psoriasis? J Eur Acad Dermatol Venereol, 2006. 20(4): p. 483-4.
Strange, A., et al., A genome-wide association study identifies new psoriasis susceptibility loci and an interaction between HLA-C and ERAP1. Nat Genet, 2010. 42(11): p. 985-90.
Sugarman, J. (2008). Epidermal Nevus Syndromes. Seminars in cutaneous medicine and surgery. 26. 221-30.
Thomas AC, Zeng Z, Riviere JB, O'Shaughnessy R, Al-Olabi L, St-Onge J et al. Mosaic Activating Mutations in GNA11 and GNAQ Are Associated with Phakomatosis Pigmentovascularis and Extensive Dermal Melanocytosis. The Journal of investigative dermatology 2016;136(4):770-8.
Tiwary A.K. MDK. A unique porokeratotic variant of inflammatory linear verrucous epidermal nevus. Indian Journal of Paediatric Dermatology 2017;18:237-40.
Unna PG. The histopathology of the diseases of the skin. New York: W. F. Clay; 1896.
Vissers WH, Muys L, Erp PE, de Jong EM, van de Kerkhof PC. Immunohistochemical differentiation between inflammatory linear verrucous epidermal nevus (ILVEN) and psoriasis. European journal of dermatology : EJD 2004;14:216-20.
Wang J, Liu Y, Liu F, Huang C, Han S, Lv Y et al. Loss-of-function Mutation in PMVK Causes Autosomal Dominant Disseminated Superficial Porokeratosis. Sci Rep 2016;6:24226.
Went, L.N., et al., X-linked ichthyosis: linkage relationship with the Xg blood groups and other studies in a large Dutch kindred. Ann Hum Genet, 1969. 32(4): p. 333-45.
Wilkinson DI, Farber EM. Free and esterified sterols in surface lipids from uninvolved skin in psoriasis. The Journal of investigative dermatology 1967;48:249-51.
Yang, H., H. Wang, and R. Jaenisch, Generating genetically modified mice using CRISPR/Casmediated genome engineering. Nat Protoc, 2014. 9(8): p. 1956-68.
Zhang Z, Li C, Wu F, Ma R, Luan J, Yang F et al. Genomic variations of the mevalonate pathway in porokeratosis. Elife 2015;4:e06322.
Atzmony, Lihi et al., "Topical cholesterol/lovastatin for the treatment of Porokeratosis: a Pathogenesis Directed Therapy", Journal of the American Academy of Dermatology, 2019, pp. 1-26.

* cited by examiner

THERAPY FOR INFLAMMATORY LINEAR VERRUCOUS EPIDERMAL NEVUS (ILVEN)

CROSS-REFERENCES TO RELATED APPLICATIONS

This application is a U.S. National Phase Application of PCT International Application No. PCT/GB2019/052409, filed Aug. 29, 2019, which is an International Application of and claims the benefit of priority to British Patent Application No. 1814036.8, filed on Aug. 29, 2018, the entire contents of which are herein incorporated by reference.

The present invention relates to the treatment of Inflammatory Linear Verrucous Epidermal Nevus (ILVEN). In particular, the treatment involves the use of a combination of an HMG-CoA reductase inhibitor and cholesterol or a precursor thereof.

BACKGROUND TO THE INVENTION

Inflammatory Linear Verrucous Epidermal Nevus (ILVEN) is a rare skin disorder of unknown aetiology that affects children at birth or in the first few years of life. It consists of inflamed, red, thickened, scaly, itchy and often painfully fissured skin, usually along lines of embryonic skin development known as Blaschko's lines. It is highly resistant to treatments of all types, whether topical, systemic, or laser. Invasive surgery as a last resort can remove some of the lesions in some patients, but in others the areas are too extensive for this to be even a last resort.

New treatments for this condition would be highly desirable. Particularly desirable would be treatment strategies based on the use either of drugs already validated for treatment of other conditions or substances known to be pharmacologically acceptable owing to their endogenous existence.

It has now surprisingly been found that a combination of an HMG-CoA reductase inhibitor and cholesterol, or a precursor thereof, may have significant efficacy in treating ILVEN. The activity of the combination therapy may in particular be higher than would be expected from the activity of either component of the combination, when used as a monotherapy. Topical administration of the combinations defined above may also avoid side effects resulting from systemic administration as well as improving efficacy at a given dosage.

The combination therapy may, in particular, be beneficial for ILVEN patients having a particular genetic profile, and specifically having one or more mutations in genes associated with cholesterol metabolism. Thus, it has now been found that the manifestation of ILVEN, at least in a proportion of cases, may be associated with genetic defects in cholesterol metabolism, or genetic defects leading to functional effects on the cholesterol metabolism process.

SUMMARY OF THE INVENTION

The present invention provides a pharmaceutical composition which comprises: (a) an HMG-CoA reductase inhibitor; and (b) cholesterol or a pharmaceutically acceptable precursor thereof, for use in treating Inflammatory Linear Verrucous Epidermal Nevus (ILVEN).

The present invention also provides an HMG-CoA reductase inhibitor for use in treating Inflammatory Linear Verrucous Epidermal Nevus (ILVEN), by co-administration with cholesterol or a pharmaceutically acceptable precursor thereof.

The present invention additionally provides cholesterol or a pharmaceutically acceptable precursor thereof for use in treating Inflammatory Linear Verrucous Epidermal Nevus (ILVEN), by co-administration with an HMG-CoA reductase inhibitor.

The present invention still further provides a method of treating a patient suffering from Inflammatory Linear Verrucous Epidermal Nevus (ILVEN) which method comprises co-administering to said patient (a) an HMG-CoA reductase inhibitor, and (b) cholesterol or a pharmaceutically acceptable precursor thereof.

Also provided by the present invention is a product comprising (a) an HMG-CoA reductase inhibitor, and (b) cholesterol or a pharmaceutically acceptable precursor thereof, as a combined preparation for simultaneous, concurrent, separate or sequential use in the treatment of a patient suffering from or susceptible to Inflammatory Linear Verrucous Epidermal Nevus (ILVEN).

Furthermore, the present invention provides the use of (a) an HMG-CoA reductase inhibitor in the manufacture of a medicament for the treatment of Inflammatory Linear Verrucous Epidermal Nevus (ILVEN) by co-administration with (b) cholesterol or a pharmaceutically acceptable precursor thereof.

The present invention additionally provides use of (b) cholesterol or a pharmaceutically acceptable precursor thereof in the manufacture of a medicament for the treatment of Inflammatory Linear Verrucous Epidermal Nevus (ILVEN) by co-administration with (a) an HMG-CoA reductase inhibitor.

DETAILED DESCRIPTION OF THE INVENTION

HMG-CoA Reductase Inhibitor

An HMG-CoA reductase inhibitor is a substance that is capable of inhibiting HMG-CoA reductase. HMG-CoA reductase is the rate-controlling enzyme of the mevalonate pathway, which produces cholesterol and other isoprenoids in vivo. HMG-CoA reductase inhibitors are commonly known as statins, and the terms HMG-CoA reductase inhibitor and statin are used interchangeably in the present disclosure.

As will be well known by those skilled in the art, statins have been widely prescribed for reducing serum cholesterol levels in patients in need thereof. For example, they have been utilised to reduce the risk of heart disease in individuals with high cholesterol, to reduce mortality in patients having existing cardiovascular disease and in various other conditions associated with undesirably high cholesterol levels.

Non-limiting examples of HMG-CoA reductase inhibitors that can be used in accordance with the present invention include atorvastatin, cerivastatin, fluvastatin, lovastatin, mevastatin, pitavastatin, pravastatin, rosuvastatin, and simvastatin, as well as pharmaceutically acceptable salts and esters thereof. Presently preferred HMG-CoA reductase inhibitors include atorvastatin, fluvastatin, pravastatin, rosuvastatin, simvastatin and lovastatin, and pharmaceutically acceptable salts and esters thereof. Particularly preferred is simvastatin and lovastatin, or a pharmaceutically acceptable salt or ester thereof. For example, the HMG-CoA reductase inhibitor may be simvastatin or lovastatin.

It is within the scope of the present invention to make use of two or more such compounds. Thus, the HMG-CoA reductase inhibitor may comprise a single active agent (i.e. a single statin) or it may comprise two or more active agents (i.e. two or more statins).

Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds for use in this invention include addition salts with a pharmaceutically acceptable acid such as such as hydrochloric acid, sulphuric acid, methanesulphonic acid, fumaric acid, maleic acid, succinic acid, acetic acid, benzoic acid, citric acid, tartaric acid or phosphoric acid. Other salts may be formed with a pharmaceutically acceptable base. Suitable such pharmaceutically acceptable salts include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

Standard principles similarly underlie the selection and preparation of pharmaceutically acceptable esters. If a HMG-CoA reductase inhibitor contains more than one hydroxyl moiety, then one or more than one (for example all) of the hydroxyl moieties may be esterified. Examples of suitable esters include $C_{1-6}$ alkynyl, alkenyl and alkyl esters or such esters in which one of the carbon atoms of the $C_{1-6}$ alkynyl, alkenyl or alkyl group (along with any hydrogen atoms to which it is attached) is replaced by phenyl. Specific examples include $C_{1-6}$ alkyl and phenyl esters, e.g. $C_{1-4}$ alkyl esters (such as methyl, ethyl, propyl, isopropyl, butyl, isobutyl or tert-butyl ester) and phenyl esters.

Cholesterol or Precursor Thereof

Cholesterol is one of the three key stratum corneum lipids (along with ceramides and free fatty acids) that form the extracellular lamellar bilayer that mediates epidermal barrier function.

Cholesterol is an endogenous sterol that has the chemical formula

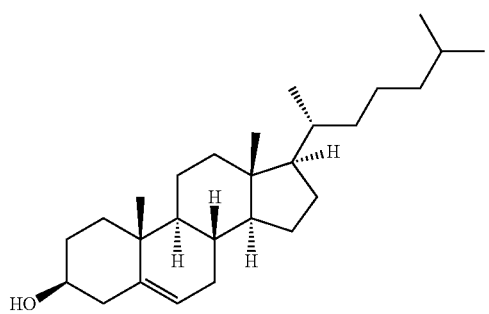

In accordance with the present invention the cholesterol is most preferably provided as such as an active ingredient. However, a pharmaceutically acceptable precursor of cholesterol can also be used, provided that such a precursor is capable of generating cholesterol in vivo in the subject after administration of the precursor.

A pharmaceutically acceptable precursor of cholesterol is a pharmaceutically acceptable substance that is capable of metabolising in order to form cholesterol after administration to a patient (i.e., in vivo). Non-limiting examples of such precursors include a prodrug of cholesterol and an intermediate in the in vivo production of cholesterol from mevalonate.

A prodrug is a (typically synthetic) derivative of cholesterol that is capable of metabolising to form cholesterol after administration. Often the prodrug of cholesterol is a compound in which the hydroxyl moiety of cholesterol is derivatised, such as esterified. Non-limiting examples of suitable prodrugs thus include a cholesterol ester, a cholesterol phosphate ester and a cholesterol sulphate ester.

The prodrug, may, for example, be a compound of the formula (I)

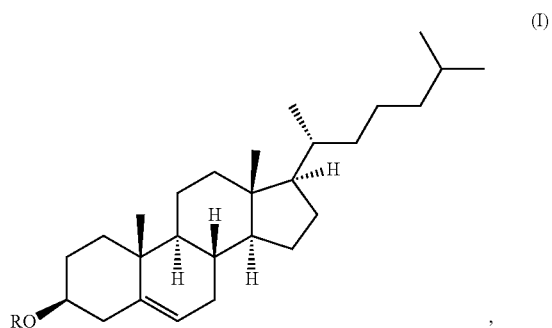

in which the group —OR is an ester group, a phosphate ester group or a sulphate ester group. One preferred class of prodrug is a cholesterol ester of formula (I), in which R is a hydrocarbyl group, for example a $C_{1-20}$ alkynyl, alkenyl or alkyl group or such a group in which one to three of the carbon atoms (along with any hydrogen atoms to which it is attached) is replaced by $C_{6-20}$ aryl. Examples include $C_{1-6}$ alkynyl, alkenyl and alkyl or such a group in which one of the carbon atoms (along with any hydrogen atoms to which it is attached) is replaced by phenyl. Specific examples include $C_{1-6}$ alkyl and phenyl, e.g. $C_{1-4}$ alkyl (such as methyl, ethyl, propyl, isopropyl, butyl, isobutyl or tert-butyl ester) and phenyl.

An intermediate in the in vivo production of cholesterol from mevalonate is an endogenous cholesterol precursor compound. The biosynthetic pathway by which cholesterol is produced in vivo from mevalonate is well understood and proceeds via a well known cascade of chemical reactions and intermediate compounds. Any intermediate compound in this well known biosynthetic pathway can be utilised as the intermediate in accordance with the present invention.

Examples of such intermediates that can be used in accordance with the invention include mevalonate itself (and mevalonic acid), mevalonate-5-phosphate, mevalonate pyrophosphate, isopentyl pyrophosphate (IPP), dimethylallyl pyrophosphate (DMAPP), geranyl pyrophosphate, farnesyl pyrophosphate, squalene, 2,3-oxidosqualene, lanosterol, 4,4-dimethylcholesta-8(9),14,24-trien-3β-ol, 4,4-dimethylcholesta-8(9),24-dien-3β-ol, zymosterol, cholesta-7,24-dien-3β-ol, cholesta-5,7,24-trien-3β-ol, desmosterol, 4,4,14α-trimethylcholesta-8(9)-en-3β-ol, 4,4-dimethylcholesta-8(9),14-dien-3β-ol, 4,4-dimethylcholesta-8(9)-en-3β-ol, cholesta-8(9)-en-3β-ol, lathosterol and 7-dehydrocholesterol. Pharmaceutically acceptable salts and esters of these compounds are also considered to be suitable intermediates within this disclosure. Examples of suitable salts and esters are the same as those disclosed elsewhere herein with reference to the HMG-CoA reductase inhibitor and the cholesterol prodrug.

Combination of Active Ingredients

The present invention involves the use of a combination of (a) an HMG-CoA reductase inhibitor, and (b) cholesterol or a pharmaceutically acceptable precursor thereof.

Such a combination of active ingredients has previously been reported to have a positive effect in a compassionateuse treatment of patients with CHILD syndrome (Kiritsi et al., Orphanet Journal of Rare Diseases 2014 9:33).

CHILD syndrome is a separate condition from ILVEN in terms of clinical classification and general understanding amongst dermatologists. It was described in 1980 and is most classically a dramatic disease where half the child is covered in red scaly skin, and the same side of the body has congenitally absent or malformed limbs. The skin findings in CHILD syndrome are generally classified as a type of ichthyosis, which is also known as Mendelian disorders of cornification or MEDOC, a large and very heterogeneous group of conditions all of which produce scaly+/−red skin. It can however be mild, with only Blaschko-linear scaly skin, which would usually then be called an epidermal naevus in the absence of a family history of CHILD (for example this type of localised skin change is often found in an unsuspecting mother of a child with CHILD syndrome). Since 2000, it has been known that the genetic cause of CHILD syndrome is a germline mutation in the gene NSDHL, which is involved in cholesterol biosynthesis.

Importantly, the skin findings in CHILD have been described as highly specific for the condition, even being designated as the "CHILD naevus" by the clinician who originally described the syndrome, and specifically separated from a diagnosis of ILVEN, amongst other differentials. The most characteristic histological feature is said to be foamy histiocytes in the papillae ("verruciform xanthoma").

The genetics of ILVEN have not previously been explored systematically. For example, unlike CHILD, ILVEN has not previously been proposed to be a disorder of the cholesterol pathway or linked to a defect in normal cholesterol metabolism. The vast majority of described cases have been sporadic, suggesting a post-zygotic mutational event; however, very rarely familial cases in mother and daughter have been described.

Furthermore, the authors of the Kiritsi et al. paper found that the same composition was ineffective in the treatment of at least two other MeDOC conditions closely related to CHILD (namely, X-linked recessive ichthyosis and Autosomal recessive congenital ichthyosis), suggesting a potentially narrow applicability of the composition.

The efficacy of the present combination in the treatment of ILVEN is therefore surprising in view of the previous state of the art. Without being limited to theory, it is considered that the efficacy of the present combination therapy in treating ILVEN may be linked to the patient group in question having abnormal cholesterol metabolism (i.e., as a consequence of a mutation in one or more genes associated with cholesterol metabolism). The present invention is also, in part, based on the novel hypothesis that the clinical features in CHILD may in some cases be similar to ILVEN, and that the treatment described by Kiritsi et al. might therefore potentially have utility in treatment of ILVEN.

In one aspect, the present invention provides a pharmaceutical composition which comprises: (a) an HMG-CoA reductase inhibitor; and (b) cholesterol or a pharmaceutically acceptable precursor thereof, the pharmaceutical composition being for use in treating ILVEN. Pharmaceutical compositions according to the invention will typically further comprise one or more pharmaceutically acceptable excipients or carriers.

Typically the patient to be treated is a mammal. Preferably the patient is a human.

It will be appreciated that not all patients suffering from a particular condition (e.g. ILVEN) will necessarily experience substantial therapeutic benefits as a result of the present combination therapy. For the avoidance of doubt, it is not essential to the invention that every patient clinically diagnosed with ILVEN be susceptible to such treatment. Indeed, it is well established across the medical field as a whole that valuable therapeutic strategies will in general function more successfully in some patients than in others (and that in some patients, within the patient population as a whole, substantially no benefit may be observed). The combination therapy of the present invention provides a valuable alternative therapeutic strategy for the treatment of IVLEN.

Particularly preferred patients to be treated are those having functionally abnormal cholesterol metabolism in the skin. A patient having abnormal cholesterol metabolism may, for example, be defined as a patient having a mutation in one or more genes associated with cholesterol metabolism. The mutation or mutations may, in general, be in any gene or genes associated with cholesterol metabolism. Such genes are well known in the art. Without being limited by theory, the combination therapy may serve to correct cholesterol imbalances via the supply of exogenous cholesterol, as well as mitigating the deleterious effects arising from the genetic mutation(s), including but not limited to the excessive formation of cholesterol precursors, by-products, or other related compounds, via the inhibition of HMG-CoA reductase and the resulting inhibition of the cholesterol pathway.

The mutation in one or more genes associated with cholesterol metabolism may result in the gene in question having abnormally enhanced expression of its coded protein or abnormally suppressed expression of its coded protein. The mutation may be any change with respect to the relevant human genome reference sequence, particularly one having a functional consequence such as abnormally enhanced expression of its coded protein or abnormally suppressed expression of its coded protein. For example, the mutation may be (but is not limited to being) a single nucleotide variant (SNV), multiple nucleotide variant, a deletion mutation, an insertion mutation, a translocation, a missense mutation or a splice site mutation resulting in a change in the amino acid sequence (coding mutation).

The one or more genes associated with cholesterol metabolism may, for example, be one or more genes selected from the genes listed in Table 1.

TABLE 1

AACS
AAGAB
ABCA1
ABCA12
ABCA13
ABCA2
ABCA5
ABCA7
ABCB4
ABCG1
ABCG4
ABCG5
ABCG8
ABHD5
ACAA2
ACADL
ACADVL
ACLY
ACSM1
ACSM3
ADAM17
ADIPOQ
AGMO
AGT
AGTR1
AKR1C1

TABLE 1-continued

| |
|---|
| AKR1D1 |
| ALDH3A2 |
| ALOX12B |
| ALOXE3 |
| AMPD2 |
| ANGPTL3 |
| ANXA6 |
| AP1S1 |
| APOA1 |
| APOA2 |
| APOA4 |
| APOA5 |
| APOB |
| APOBR |
| APOC1 |
| APOC2 |
| APOC3 |
| APOD |
| APOE |
| APOF |
| APOL1 |
| APOL2 |
| APOM |
| APP |
| AQP5 |
| ARSE |
| ARV1 |
| BCL10 |
| C14orf1 |
| CAD |
| CARD11 |
| CARD14 |
| CASP14 |
| CAT |
| CAV1 |
| CAV3 |
| CBR3 |
| CCL3 |
| CCR5 |
| CD24 |
| CD36 |
| CDSN |
| CEBPA |
| CEL |
| CELA3A |
| CELA3B |
| CERS3 |
| CES1 |
| CETP |
| CFTR |
| CH25H |
| CHUK |
| CLDN1 |
| CLN6 |
| CLN8 |
| CLU |
| CNBP |
| CPS1 |
| CSTA |
| CTSC |
| CUBN |
| CYB5R1 |
| CYB5R2 |
| CYB5R3 |
| CYP11A1 |
| CYP11B1 |
| CYP11B2 |
| CYP17A1 |
| CYP19A1 |
| CYP1B1 |
| CYP21A2 |
| CYP26B1 |
| CYP27A1 |
| CYP2C9 |
| CYP39A1 |
| CYP46A1 |
| CYP4F22 |
| CYP4V2 |
| CYP51A1 |
| CYP7A1 |

TABLE 1-continued

| |
|---|
| CYP7B1 |
| CYP8B1 |
| DGAT1 |
| DGAT2 |
| DHCR24 |
| DHCR7 |
| DHRS4 |
| DISP3 |
| DPYD |
| DSC2 |
| DSC3 |
| DSG1 |
| DSG2 |
| DSG4 |
| DSP |
| DYNAP |
| EBP |
| EBPL |
| EGF |
| EHD1 |
| EIF2A |
| ELOVL4 |
| EPHX2 |
| ERLIN1 |
| ERLIN2 |
| F7 |
| FABP3 |
| FABP4 |
| FADS1 |
| FAXDC2 |
| FBXW7 |
| FDFT1 |
| FDPS |
| FDX1 |
| FDX1L |
| FDXR |
| FGF1 |
| FGFR4 |
| G6PC |
| G6PD |
| GART |
| GGPS1 |
| GJB2 |
| GMPS |
| GPIHBP1 |
| GPLD1 |
| GPR183 |
| HDLBP |
| HMGCR |
| HMGCS1 |
| HMGCS2 |
| HNF4A |
| HSD17B7 |
| IDI1 |
| IDI2 |
| IKBKB |
| IKBKG |
| IL18 |
| IL4 |
| INHBA |
| INSIG1 |
| INSIG2 |
| JUP |
| KANK2 |
| KRT1 |
| KRT10 |
| KRT2 |
| KRT6C |
| KRT9 |
| LAMTOR1 |
| LBR |
| LCAT |
| LDLR |
| LDLRAP1 |
| LEP |
| LEPR |
| LIPA |
| LIPC |
| LIPE |
| LIPG |

TABLE 1-continued

LIPN
LMF1
LMNA
LOR
LPL
LRP1
LRP5
LRP6
LRP8
LSS
LYN
MALL
MALRD1
MALT1
MAP3K7
MBTPS1
MBTPS2
MED13
MIA2
MLC1
MSMO1
MSR1
MT3
MVD
MVK
MYLIP
NCEH1
NFKB1
NFKBIA
NIPAL4
NPC1
NPC1L1
NPC2
NR0B2
NR1D1
NR1H2
NR1H3
NR1H4
NR5A2
NSDHL
NUS1
OSBP
OSBP2
OSBPL10
OSBPL1A
OSBPL2
OSBPL3
OSBPL5
OSBPL7
OSBPL8
PCSK9
PDPK1
PEX7
PHYH
PKP1
PKP2
PLA2G10
PLA2G15
PLSCR3
PLTP
PMP2
PMVK
PNLIP
PNPLA1
POL32F
POMP
PON1
POR
PPARA
PPARD
PPARG
PRKAA1
PRKAA2
PRKAG2
PRKCQ
PROM2
PTCH1
RALY
RHBDF2
RIPK4

TABLE 1-continued

RORA
RORC
RXRA
SASH1
SC5D
SCAP
SCARB1
SCARF1
SCP2
SCP2D1
SEC14L2
SEC24A
SERPINA12
SHH
SIRT1
SLC27A4
SLURP1
SMAD2
SMO
SNAP29
SNX17
SOAT1
SOAT2
SOD1
SORL1
SPINK5
SQLE
SRD5A2
SREBF1
SREBF2
ST14
STAR
STARD3
STARD4
STARD5
STARD6
STS
STX12
SYP
SYT7
TGFB1
TGFBR1
TGFBR2
TGM1
TM7SF2
TMEM97
TNFSF4
TRAF6
TRERF1
TRPV3
TSPO
TSPO2
UMPS
URS00000E5433_9606
URS000013D17D_9606
URS0000272039_9606
USF1
USF2
VLDLR
VPS33B
VPS4A
VPS4B
XBP1
ZND750

All of the genes listed in Table 1 are known to be associated with cholesterol metabolism. In preferred aspects of the invention, the patients to be treated may have abnormal cholesterol metabolism. More preferably the patients to be treated may have a mutation in one or more genes associated with cholesterol metabolism (e.g. a mutation in one or more of the genes listed in Table 1). More preferably still the patients to be treated may have a mutation in one or more genes selected from the group consisting of PMVK, TGFB1, TGM1 and NSDHL. More preferably still the patients to be treated may have a mutation in one or more genes selected from the group consisting of NSDHL, TGFB1 and TGM1. More preferably still the patients to be treated may have a mutation in the NSDHL or TGFB1 gene. Most preferably the patients to be treated may have a mutation in the TGFB1 gene. Thus, the patient may have a mutation in the PMVK gene. The patient may have a mutation in the TGFB1 gene. The patient may have a mutation in the TGM1 gene. The patient may have a mutation in the NSDHL gene. Some specific gene mutations of interest are disclosed in the examples section of this application (see Table 3).

The mutation is typically a causative mutation. Causative mutations are genetic mutations occurring in genes that have a causative effect on a trait or condition in a subject. A causative mutation in the context of the present invention thus means a genetic mutation that contributes to or results in the manifestation of ILVEN in the subject. The subject to be treated in the present invention may have such a causative mutation. The causative mutation is typically a mosaic mutation; it is present in affected tissue, but not in unaffected tissue.

Causative mutations for ILVEN may, for instance, be identified by taking biopsies and demonstrating that the mutation is present in affected, but not unaffected, skin. The mutations can be identified using methods known in the art such as by whole exome sequencing.

The subject to be treated may have at least one causative mutation that contributes to or results in the manifestation of ILVEN in the subject. For the avoidance of doubt, references herein to the presence of "a" or "the" mutation do not exclude the possibility that the subject exhibits a plurality of mutations, e.g. two or more causative mutations. The or each mutation is typically a mosaic mutation.

The mutation may be a gain-of-function mutation or a loss-of-function mutation. The mutation is preferably a mutation in a gene that modulates/alters cholesterol metabolism. Modulating/altering cholesterol metabolism may mean dysregulation therein, such as but not limited to insufficient cholesterol production, or excessive cholesterol production, or insufficient or excessive production of one or more metabolic cholesterol precursors.

Furthermore, homologues of the genes and proteins described herein may also be used in the present disclosure, i.e. they may also represent the gene or genes that are subject to a causative mutation(s) in the subject. As used herein, "homology" refers to sequence similarity between a reference sequence and at least a fragment of a second sequence. As used herein, "homology" of a gene refers to the degree of identity of two or more gene sequences to each other. Thus, the higher the homology of two genes, the higher the identity or similarity of their sequences.

Whether two genes have homology can be examined by direct comparison of sequences, or by hybridization under stringent conditions in the case of nucleic acids. Homologues may be identified by any method known in the art, preferably, by using the BLAST tool to compare a reference sequence to a single second sequence or fragment of a sequence or to a database of sequences. As described below, BLAST will compare sequences based upon percent identity and similarity.

When directly comparing two gene sequences, the DNA sequence between the gene sequences is typically at least 50% identical, preferably at least 70% identical, more preferably at least 80%, 90%, 95%, 96%, 97%, 98% or 99% identical to each other, they have homology.

As used herein, "orthologue" refers to genes in different species that derive from a common ancestor gene. Homologous genes or homologous gene products are also sometimes referred to as orthologous genes or orthologous gene products. It is understood that such homologues, homologous gene products, orthologous genes or orthologous gene products and the like can also be used so long as they conform to the object of the present invention.

The present invention extends to situations where the active ingredients discussed above are co-administered. When the active ingredients are co-administered they can be present in separate pharmaceutical compositions. Thus, for example, the HMG-CoA reductase inhibitor can be administered orally, and the cholesterol or precursor thereof can be administered topically. Alternatively the HMG-CoA reductase inhibitor can be administered topically, and the cholesterol or precursor thereof can be administered orally. Still further, both components could be administered orally or, more preferably, topically in separate pharmaceutical compositions.

In a preferred embodiment, the active ingredients are formulated into a single pharmaceutical composition. Such a pharmaceutical composition may be suitable for administration by any appropriate means, including topically and orally. For some patients with very extensive disease, it may be more practical (and/or assist with patient compliance) to utilise oral administration. Preferably, however, the composition is suitable for topical administration. Topical administration of the HMG-CoA reductase inhibitor may be advantageous since it avoids the issue of first-pass hepatic metabolism of statins following systemic administration. Topical administration of the cholesterol or precursor thereof may also be advantageous since it avoids the issue of incorporation of systemically delivered compound into lipoprotein particles, which are unable to access peripheral tissues without LDL receptors, such as the epidermis.

For the avoidance of doubt, in the product comprising (a) an HMG-CoA reductase inhibitor, and (b) cholesterol or a pharmaceutically acceptable precursor thereof, as a combined preparation for simultaneous, concurrent, separate or sequential use in the treatment of a patient suffering from or susceptible to ILVEN, the product may comprise either a single pharmaceutical composition that comprises both (a) and (b) or alternatively a first pharmaceutical composition that comprises (a) and a second (i.e., separate) pharmaceutical composition that comprises (b).

Co-administration of the active ingredients according to the present invention includes simultaneous, separate and sequential administration. Typically, both drugs are administered simultaneously or one drug is administered first and the second drug is administered within 12 hours, preferably within 6 hours, more preferably within 3 hours, most preferably within 1 hour after the administration of the first drug, Typically, the active ingredients are applied topically to the patient, i.e. to the affected areas of the skin.

Pharmaceutical compositions according to the invention may be suitable for oral, buccal, nasal, topical, ophthalmic or rectal administration. Preferably, the compositions are suitable for topical administration.

For oral administration, the pharmaceutical compositions of the present invention may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

For ophthalmic administration the pharmaceutical compositions of the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the pharmaceutical compositions of the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

For topical administration the pharmaceutical compositions of the present invention may take the form of any formulation normally used for topical administration, in particular solutions, lotions, emulsions of liquid consistency, emulsions of semi-liquid consistency, emulsions of semi-solid consistency, emulsions of solid consistency, creams, gels or ointments. The emulsions are obtained by dispersion of an oil phase in water (O/W) or a water phase in oil (W/O). For example, some pharmaceutical compositions for topical administration contain an oil phase. Such pharmaceutical compositions may, for example, be water-in-oil emulsions (i.e. emulsions wherein the water is the dispersed phase and the oil in the dispersion medium) or be substantially non-aqueous.

Compositions for topical use in accordance with the invention may also contain one or more emollients, emulsifiers, thickeners and/or preservatives. The emollients are typically long chain alcohols, such as cetyl alcohol, stearyl alcohol and cetearyl alcohol; hydrocarbons such as petrolatum and light mineral oil; or acetylated lanolin. The total amount of emollient in the formulation is preferably about 5% to about 30%, and more preferably about 5% to about 10% by weight based on the total weight of the formulation. The emulsifier is typically a nonionic surface active agent, e.g., polysorbate 60 (available from Sigma Aldrich), sorbitan monostearate, polyglyceryl-4 oleate, and polyoxyethylene (4)lauryl ether or trivalent cationic. Generally the total amount of emulsifier is preferably about 2% to about 14%, and more preferably about 2% to about 6% by weight based on the total weight of the formulation. Pharmaceutically acceptable thickeners, such as Veegum.TM.K (available from R. T. Vanderbilt Company, Inc.), and long chain alcohols (i.e. cetyl alcohol, stearyl alcohol or cetearyl alcohol) can be used. The total amount of thickener present is preferably about 3% to about 12% by weight based on the total weight of the formulation. Preservatives such as methylparaben, propylparaben and benzyl alcohol can be present in the formulation.

Optionally, an additional solubilizing agent such as benzyl alcohol, lactic acid, acetic acid, stearic acid or hydrochloric acid can be included in the formulation. If an additional solubilizing agent is used, the amount present is preferably about 1% to about 12% by weight based on the total weight of the cream.

Optionally, the formulation can contain a humectant such as glycerin and skin penetration enhancers such as butyl stearate.

It is known to those skilled in the art that a single ingredient can perform more than one function in a composition, i.e., cetyl alcohol can serve both as an emollient and as a thickener.

The pharmaceutical composition of the invention optionally comprises an oil phase. In this case, typically the amount of oil in the composition is at least 10 wt. %, preferably at least 30 wt. %, more preferably at least 50 wt. %, more preferably at least 80 wt. %, based on the total weight of the composition. As used herein an oil phase is typically a liquid or solid phase which is substantially immiscible with water. More typically, an oil phase as used herein has a solubility in water at 25° C. of less than or equal to 1 mg/L, preferably less than 0.1 mg/L.

The oil phase in an emulsion may be any oil phase normally used in emulsions for topical administration. Such oil phases include, for example, hydrocarbon bases such as such as hard paraffin, soft paraffin, ceresine and microcrystalline wax, absorption bases such as lanolin and beeswax, emulsifying bases such as emulsifying wax and cetrimide, and vegetable oils such as olive oil, coconut oil, sesame oil, almond oil and peanut oil. Other oil phases useful in accordance with the invention are mineral oil, liquid petroleum, sorbitan monostearate, polysorbate 60, cetyl esters wax, cetearyl alcohol, benzyl alcohol and 2-octyldodecanol.

Those skilled in the art will understand that by varying the ratio of water to oil in an emulsion, the result could be deemed a lotion, a cream, or an ointment, by order of increasing proportion of oil. An emulsion comprising similar proportions of oil phase and water phase is usually deemed a cream, whereas an ointment will generally contain a substantially higher proportion of oil phase compared to water phase, for example greater than 60 wt. % oil phase, preferably greater than 70 wt. % oil phase, more preferably greater than 80 wt. % oil phase, based on the total weight of the oil phase and the water phase. A lotion will generally contain a lower proportion of oil phase than a cream, for example under 25 wt. % oil phase, under 20 wt. % oil phase, under 15 wt. % oil phase, under 10 wt. % oil phase or under 5 wt. % oil phase, based on the total weight of the oil phase and the water phase.

Generally, a cream for use according to the invention comprises an oil phase and a water phase mixed together to form an emulsion. Preferably, the amount of water present in a cream of the invention is about 45% to about 85% by weight based on the total weight of the cream, more preferably about 45 wt. % to about 65 wt. %, even more preferably about 45 wt. % to about 55 wt. %.

Where the composition is an ointment a pharmaceutically acceptable ointment base will be used. Examples of ointment bases include hydrocarbon bases such as such as hard paraffin, soft paraffin, ceresine and microcrystalline wax, absorption bases such as lanolin and beeswax, water-soluble bases such as polyethylene glycols (e.g. polyethylene glycol 200, 300, 400, 3350, 4000 or 6000), propylene glycol and polypropylene glycols, emulsifying bases such as emulsifying wax and cetrimide, and vegetable oils such as olive oil, coconut oil, sesame oil, almond oil and peanut oil. Mixtures of ointment bases can of course be used. The amount of ointment base present in an ointment of the invention is preferably about 60% to about 95% by weight based on the total weight of ointment, more preferably about 70 wt. % to about 90 wt. %, still more preferably about 75 wt. % to about 85 wt. %.

The pharmaceutical composition for use in accordance with the present invention may also be a lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

Specific exemplary, but non-limiting compositions include those in which the two active ingredients are incorporated into the following topical vehicles: (i) a vehicle comprising macrogol stearate 400, glycol. Monostearate 44-50, sorbitan monostearate and petroleum jelly (e.g., Unguentum Cordes®, which is an amphiphilic, hypoallergenic vehicle); and (ii) paraben-preserved water.

In the compositions and products according to the invention, the HMG-CoA reductase inhibitor and the cholesterol or pharmaceutically acceptable precursor thereof may each be present at a concentration of between 0.001 and 20% by weight, relative to the total weight of the composition or product, preferably between 0.01 and 10%, more preferably between 0.02 and 5% by weight, and more preferably still between 1 and 4% by weight. In a particular embodiment, each of the two active ingredients is present at a concentration of between 1 and 3% by weight (e.g. approximately 2% by weight of cholesterol and between 2% by weight of simvastatin or lovastatin).

The present invention is explained in more detail in the following by referring to Examples, which are not to be construed as limitative.

EXAMPLES

Example 1

Methods

Fourteen patients with ILVEN were recruited. Photographs were taken of all cases as a baseline. DNA was extracted directly from lymphocytes and from affected skin biopsy without culture, using standard methods. Where possible a second skin biopsy of affected skin was also obtained for primary keratinocyte culture and immortalization with HPV to establish a stable cell line. In a minority of cases a skin biopsy of normal skin was also taken for keratinocyte culture and immortalization. Histopathology of affected skin was obtained in all cases. Information about the patients is summarised in Table 2 below.

TABLE 2

| Patient number | Sex | Phenotype | Response to topical cholesterol/simvastatin |
|---|---|---|---|
| 1 | Female | Localised right-sided ILVEN - minor phenotypic presentation of CHILD syndrome | Clear and maintained response, likely to lead to total resolution given genetic defect |
| 2 | Male | Extensive bilateral ILVEN; whole body | Clear and maintained improvement. |
| 3 | Female | Localised ILVEN; right leg | Minor response, not maintained |
| 4 | Female | Extensive bilateral ILVEN; whole body | None |
| 5 | Male | Extensive bilateral ILVEN; whole body | Minor response, not maintained. |
| 6 | Female | Left sided ILVEN; groin and left hand | Was biopsied before cream available, then lost to follow up |
| 7 | Female | Localised ILVEN; left leg, plus possible psoriasis on abdomen which comes and goes | Improvement at 3 months, continuing to try |
| 8 | Male | Localised left ILVEN | Improvement at 3 months, continuing to try |
| 9 | Female | Localised ILVEN; left arm | No response, so tried cholesterol only, no response |
| 10 | Female | Localised ILVEN; left leg | No response but was od, now bd being tried for 3 months |
| 11 | Male | Extensive bilateral ILVEN; whole body | Minor response, stopped treatment |
| 12 | Female | Localised ILVEN; left arm and left upper back | Good response, lost to follow up, recontacted and restarted treatment, review in 8 weeks |
| 13 | Female | Localised ILVEN; right leg and chin | Improvement at 3 months, continuing to try |
| 14 | Female | Localised ILVEN; left arm - minor phenotypic presentation of CHILD syndrome | Clear and maintained response, likely to lead to total resolution given genetic defect |

Thirteen of the fourteen patients were treated with 200 cholesterol/2% simvastatin in Unguentum Merck, applied topically twice a day for a minimum period of three months in the first instance, and only applied to one designated area of affected skin, using the rest of the skin as an internal control. If there was no response in this time the treatment was stopped. Where there was a positive response the treatment has been continued, and extended gradually to different body areas.

DNA from blood and affected skin was sequenced using deep whole exome sequencing (WES) (mean 250× coverage, whereas the standard is often 30×). This technique has been optimized with an accompanying specific bio-informatic pipeline for the detection of mosaic mutations (as described in more detail in: (a) Thomas et al., The Journal of investigative dermatology 2016; 136(4):770-8; and (b) Kinsler et al., The Journal of investigative dermatology 2014; 134:2658-60). This is because these mutations are usually heterozygous (having occurred as a single mutation in utero), and are only carried in certain cell types, leading to a low mutant allele load which could be otherwise undetected or disregarded by normal next generation sequencing (NGS) methods. Usually it is expected that the mutations being sought will not be present in the blood and so this is used this as a comparator for finding the gene in the skin. In this disease however, on the basis of suspicions about the origin of Blaschko's lines, and the data on the last common ancestor of ectodermal and mesenchymal cells being the fertilised egg (Ju et al., Nature 2017; 543:714-8), mutations were sought that were also present at mosaic levels in the blood in those patients with widespread disease. In those with limited disease the original model was expected; however, a second hit in a recessive genetic model was also strongly suspected for some cases as most ichthyosis is recessive. A thorough analysis by many different methods was therefore performed.

Results

Of the fourteen patients, one (patient 6 in Table 1) did not have the topical therapy with cholesterol/simvastatin as she was biopsied before commencement of the trial, and was then lost to follow up. Of the thirteen treated patients, three had clear and prolonged improvement (patients 1, 2 and 14 in Table 1), and a fourth had clear improvement at three months (patient 13 in Table 1). One patient showed a good response but was lost to follow up and has now restarted treatment (patient 12 in Table 1). Six did not have a clear or prolonged response: five stopped the treatment (patients 3, 4, 5, 9 and 11 in Table 1), while the remaining one is, at the time of writing, still on a trial as they had only used it once a day instead of twice in the first three months (patient 10 in Table 1). The remaining two patients showed some improvement at three months and are continuing treatment (patients 7 and 8 in Table 1). Whole exome sequencing results have been obtained for twelve of the fourteen patients. Results are summarised in Table 3 below.

TABLE 3

| Patient number | Candidate genes | Mutation coordinates and predicted amino acid change | Genetic mechanism |
|---|---|---|---|
| 1 | NSDHL | ChrX: 15034432, p. G205C | Germline heterozygous missense, X-linked dominant Considered likely to be causal |
| 2 | PMVK TGFB1 | Chr1: 154904861, p. G7fs*25 chr19: 41,836,976G>A; c. 11544G>A, p. R385H | Germline mosaic nonsense, autosomal dominant Further studies indicated that TGFB1 is the causative gene (by taking two new biopsies and demonstrating the mutation present in affected but not unaffected skin) |
| 3 | TGM1 | Chr14: 24725217, p. D490G germline, Chr14: 24731027 p. E127* somatic, as yet unconfirmed | Germline heterozygous missense (known pathogenic) with mosaic heterozygous nonsense in skin (autosomal recessive) Considered likely this is causal in association with a second somatic hit, but this has not yet been confirmed, further sequencing is being carried out by a different method |
| 4 | CARD14 | Chr17: 78157718, p. M119K | Germline mosaic missense autosomal dominant (known pathogenic) Considered highly likely this is causal |
| 5 | CARD14 | Chr17: 80182718, c. 277A>G, p. K93E | Germline mosaic missense autosomal dominant (predicted likely pathogenic in silico) Considered highly likely this is causal |
| 6 | Under investigation | | |
| 7 | Under investigation | | |
| 8 | Under investigation | | |

TABLE 3-continued

| Patient number | Candidate genes | Mutation coordinates and predicted amino acid change | Genetic mechanism |
|---|---|---|---|
| 9 | Under investigation | | |
| 10 | Under investigation | | |
| 11 | Under investigation | | |
| 12 | Under investigation | | |
| 13 | Under investigation | | |
| 14 | NSDHL | ChrX: 152034422, p. H201fs*69 | Germline frameshift deletion, considered likely to be causal |

Patients 1 and 14 were found to carry a germline mutation in NSDHL. This indicates that some patients presenting with symptoms of, and being clinically diagnosable with, ILVEN have a germline mutation in NSDHL.

In patient 2 a mosaic mutation was found in the gene PMVK. A mutation was also found in TGFB1.

In patient 3 a germline and a mosaic skin-only mutation was found in TGM1.

In patient 4 (who had no response to treatment) and patient 5, a mosaic mutation was found in CARD14.

NSDHL, PMVK and CARD14 mutations have been excluded in the other patients where genetic data is already available, as have mutations in EBP, another X linked gene known cause Blaschko-linear disease in another condition of cholesterol metabolism Conradi-Hunnerman disease, MVK, MVD, FDPS, SLC17A9, SSH1, and SART2 (other genes on the mevalonate pathway with PMVK), and CARD11, a homologue of CARD14.

Example 2

Experiments to compare the level of cholesterol in ILVEN patients against non-ILVEN controls were performed. Filipin III was used as a cholesterol stain as it is highly fluorescent and binds specifically to cholesterol. ILVEN patients were shown to have (statistically significant) lower average levels of cholesterol than non-ILVEN controls.

The invention claimed is:

1. A method of treating a patient suffering from Inflammatory Linear Verrucous Epidermal Nevus (ILVEN) which method comprises co-administering to said patient (a) an HMG-CoA reductase inhibitor, and (b) cholesterol or a pharmaceutically acceptable precursor thereof, wherein said patient has a mutation in one or more genes associated with cholesterol metabolism.

2. A method according to claim 1, wherein said patient has a mutation in one or more genes selected from the group consisting of TGFB1, NSDHL, TGM1, and PMVK.

3. A method according to claim 1, wherein said patient has a mutation in the TGFB1 gene.

4. A method according to claim 1, wherein said patient has a mutation in the NSDHL gene.

5. A method according to claim 1, wherein said patient has a mutation in the TGM1 gene.

6. A method according to claim 1, wherein said patient has a mutation in the PMVK gene.

7. A method according to claim 1, wherein the HMG-CoA reductase inhibitor is selected from the group consisting of simvastatin, lovastatin, atorvastatin, cerivastatin, fluvastatin, mevastatin, pitavastatin, pravastatin, rosuvastatin, and a pharmaceutically acceptable salt or ester of any one of foregoing.

8. A method according to claim 1, wherein the HMG-CoA reductase inhibitor is selected from the group consisting of simvastatin, lovastatin, atorvastatin, fluvastatin, pravastatin, rosuvastatin, and a pharmaceutically acceptable salt or ester of any one of foregoing.

9. A method according to claim 1, wherein the HMG-CoA reductase inhibitor is selected from the group consisting of simvastatin, lovastatin, a pharmaceutically acceptable salt or ester of simvastatin, and a pharmaceutically acceptable salt or ester of lovastatin.

10. A method according to claim 1, wherein the cholesterol or a pharmaceutically acceptable precursor thereof is selected from the group consisting of cholesterol, a prodrug of cholesterol, and an intermediate in the in vivo production of cholesterol from mevalonate.

11. A method according to claim 1, wherein the cholesterol or a pharmaceutically acceptable precursor thereof is cholesterol.

12. A method according to claim 1, wherein the HMG-CoA reductase inhibitor is simvastatin or lovastatin and the cholesterol or a pharmaceutically acceptable precursor thereof is cholesterol.

13. A method according to claim 1, wherein the co-administering comprises simultaneously administering the HMG-CoA reductase inhibitor and the cholesterol or a pharmaceutically acceptable precursor thereof.

14. A method according to claim 1, wherein the co-administering comprises topically administering the HMG-CoA reductase inhibitor and the cholesterol or a pharmaceutically acceptable precursor thereof.

15. A method according to claim 14, wherein the co-administering comprises topically administering a pharmaceutical composition that comprises both the HMG-CoA reductase inhibitor and the cholesterol or a pharmaceutically acceptable precursor thereof.

* * * * *